United States Patent [19]

Sundelin et al.

[11] Patent Number: 4,466,823

[45] Date of Patent: Aug. 21, 1984

[54] CONTROL OF UNWANTED SICKLEPOD PLANTS

[75] Inventors: Kurt G. R. Sundelin; Gene A. Bozarth, both of Modesto, Calif.

[73] Assignee: Shell Oil Company, Houston, Tex.

[21] Appl. No.: 552,957

[22] Filed: Nov. 18, 1983

[51] Int. Cl.$^3$ ............................................ A01N 37/10
[52] U.S. Cl. ........................................ 71/115; 71/107; 562/401; 562/402; 562/459
[58] Field of Search .......................................... 71/115

[56] References Cited

U.S. PATENT DOCUMENTS

| 2,322,760 | 6/1943 | Lontz | 71/115 |
|---|---|---|---|
| 2,394,916 | 2/1946 | Jones | 71/115 |
| 2,498,302 | 2/1950 | Sexton et al. | 71/115 |
| 4,265,654 | 5/1981 | Takematsu et al. | 71/86 |
| 4,382,812 | 5/1983 | Takematsu et al. | 71/86 |
| 4,383,848 | 5/1983 | Szucs | 71/88 |

FOREIGN PATENT DOCUMENTS 0006608  1/1980  European Pat. Off. ............... 71/88

OTHER PUBLICATIONS

Kohler et al., "Ketonic Nitriles and Theik, etc.;" (1924), CA 18, pp. 2167–2168, (1924).
Vester et al., "Response of Peanuts, etc.;" (1974), CAB (Commonwealth Ag. Bureau) No. 438,302, (1974).
Waldrop et al., "Interactions of Postemergence, etc.;" (1981), CAB No. 1,655,231, (1981).
Batianoff et al., "Dynamics and Control, etc.;" (1973), CA 80, No. 1127z, (1974).

Primary Examiner—Glennon H. Hollrah

[57] ABSTRACT

Unwanted sicklepod plants are controlled by subjecting the plants to an effective dosage of the (R*,S*)-(+)-optical isomer of 4-benzoyl-2,3-diphenylbutyric acid.

1 Claim, No Drawings

CONTROL OF UNWANTED SICKLEPOD PLANTS

DESCRIPTION OF THE INVENTION

It has been found that the (R*,S*)-(+)- optical isomer of 4-benzoyl-2,3-diphenybutyric acid is toxic to sicklepod (*Cassia obtusifolia*) plants. Accordingly, this discovery provides a method for controlling unwanted sicklepod plants which comprises subjecting the plants to an effective dosage of the (R*,S*)-(+)- optical isomer of 4-benzoyl-2,3-diphenylbutyric acid (which isomer for brevity will be referred to hereinafter as Compound A), or a salt thereof.

It also has been found that the herbicidal effect of Compound A is highly selective, Compound A having little or no effect upon other species of plants to which it has been applied.

4-Benzoyl-2,3-diphenylbutyric acid is a known compound, and is known to exist in two isomeric forms, one melting at about 186° C. and one melting at about 260° C.: S. Avery and G. C. Jorgensen, Journal of the American Chemical Society, volume 52, pages 3628–3633 (1930), at page 3632. It has been established that the two isomers are diastereomers, the lower melting isomer having the threo configuration (R. B. Meyer and C. R. Hauser, Journal of Organic Chemistry, volume 27, pages 1067–9 (1962)), and the higher melting isomer having the erythro configuration (applicants). It has been found that the erythro isomer is highly active with respect to sicklepod, and that the threo isomer is much less active. Further, applicants recognzed that the erythro isomer is a racemic mixture, have resolved the enantiomers and found that the (+)- isomer (i.e., Compound A) is the active agent, the (−)- isomer being essentially inactive. The method of this invention contemplates both isolated Compound A, and mixtures thereof with the other isomers—for example, mixtures of the isomers resulting from the method of preparation and/or the method of separation of the isomers. Particular mixtures contemplated are mixtures of the threo and erythro diastereomers resulting from the method of preparation, and the erythro diastereomer isolated therefrom.

Suitable salts are those of alkali metals, alkaline earth metals, ammonia and amines, such as the salts of mono-, di- and tri- alkyl- and alkanol- amines wherein each alkyl moiety contains up to twenty carbon atoms, which are often used in preparing herbicidal formulations of herbicidal acids.

Compound A was prepared and isolated by applicants as follows:

4-Benzoyl-2,3-diphenylbutyric acid was prepared, and the erythro isomer (melting point: 262°–267° C.) was isolated by the methods described by Avery and Jorgensen, supra. The erythro configuration was confirmed by X-ray crystallography.

To separate the enantiomers in the erythro isomer, since the compounds involved are carboxylic acids, classical amine salt formation was employed, using chiral quinidine (Aldrich). The quinidine salts were formed by adding the erythro ester to a stoichiometric amount of quinidine in methylene chloride, evaporating the solvent and crystallizing the resulting salts of the enantiomers from hot ethyl acetate. The isomers crystallized in distinct crystalline forms, and were physically separated, then each was recrystallized from ethyl acetate. Each resulting salt was treated with dilute hydrochloric acid to spring the acid: Compound A—$[alpha]^{20}+54.4°$ (c=1.03, DMF); the (−)-isomer $[alpha]^{25}-54.2°$ (c=1.10, DMF). The enantiomeric purity of each product was determined by preparing the corresponding methyl ester using potassium fluoride and methyl iodide in dimethylformamide. The resulting esters were shown to be nearly 100% enantiomerically pure by capillary gas chromatography using a 25 m×0.25 mm (ID) glass capillary, open tube column with walls coated with L-valine as a copolymer with dimethylsiloxane and carboxyalkylmethylsiloxane (Applied Science Laboratories, Inc.). This system gave sharp resolution of the two chiral antipodes with Compound A having the longer retention time.

The sodium salt of Compound A (as the erythro diastereomer pair) was prepared as follows: 172 g of Compound A was mixed with a solution of 20 g of sodium hydroxide in one liter of water, at room temperature. The mixture was heated to 90° C. and filtered. The filtrate was held at 0° C. overnight and filtered. The solid so obtained was triturated in isopropyl alcohol and filtered, and the solid so obtained was dried at 100° C. to give the sodium salt, as white crystals.

Compound A has been found to be toxic to sicklepod plants, being effective when applied either preemergence (applied to the soil at the locus where the plants are, or will be, growing) or postemergence (applied to the foliage of the growing plants). It appears to be more effective when applied postemergence.

For application, Compound A is applied most effectively by formulating it with a suitable inert carrier or surface-active agent, or both. The invention, therefore, also includes compositions suitable for combatting unwanted plants, such compositions comprising Compound A, together with an inert carrier or surface-active agent, or both.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for examle, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloromethane, including liquefied, normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

The amount of Compound A to be used in combatting the undesired sicklepod plants will naturally depend on the condition of the plants, the degree of activity desired, the formulation used, the mode of application, the climate, the season of the year, and other variables. Also, it has been found that different strains of sicklepod differ in their susceptibility to Compound A, and this difference will have to be taken into account. Recommendations as to precise amounts are, therefore, not possible. In general, however, application to the locus to be protected of from 0.01 to 10.0 kg per hectare of Compound A will be satisfactory.

Since the surfaces of the sicklepod leaves are highly hydrophobic, to be most effective, it is essential that Compound A, or a salt thereof, be formulated so as to wet the surfaces of the leaves.

EXAMPLES OF ACTIVITY WITH RESPECT TO PLANTS

In the following examples, the species of plants that were tested were:
Barnyardgrass (watergrass)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnson grass—*Sorghum halepense*

TEST PROCEDURES

The preemergence (soil) herbicidal activity of Compound A was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |

-continued

| Rating | Meaning |
|---|---|
| 7 | Plant badly damaged, but expected to live |
| 6 | Moderate damage, but recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of Compound A was evaluated by spraying 10-day-old crabgrass plants, 13-day-old pigweed plants, 6-day-old Johnsongrass plants, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Compound A was applied as the pure enantiomer, and as the erythro diastereomer pair. Compound A (in the form of the erythro diastereomer pair) was inactive (rating: 0) with respect to all of the species of weeds except sicklepod, which had a rating of 7, preemergence and a rating of 9, postemergence. As the pure enantiomer, Compound A was inactive applied preemergence to all of the species of weeds except sicklepod (rating =8). Applied postemergence, it was inactive with respect to crabgrass, pigweed and velvetleaf, slightly active with respect to Johnsongrass (rating=2) and foxtail (rating=3) and highly active with respect to sicklepod (rating=9).

EXAMPLES OF SELECTIVITY

In the following examples, the species of plants that were tested were:
Barnyardgrass
Downy Brome
Wild oats—*Avena fatua*
Yellow foxtail
Goose grass—*Eleusine indica* L.
Yellow nutsedge—*Cyperus esculentus* L.
Cocklebur—*Xanthum pennsylvanicum*
Morning glory—*Ipomoea purpurea* L. (Roth)
Wild mustard—*Brassica kaber*
Redroot pigweed
Sicklepod
Velvetleaf
Corn—*Zea mays*
Cotton—*Gossypium hirsutum*
Rice—*Oryza sativa*
Grain sorghum—*Sorghum vulgare*
Soybeans—*Glycine max*
Sugarbeets—*Beta vulgaris*
Wheat—*Triticum aestivum*

TEST PROCEDURES

The preemergence activity of Compound A was further determined with respect to certain species of crop plants and common species of weeds, by spraying a formulation of Compound A (as the erythro diastereomer) on soil in small pots in which seeds of the plants had been sown. The postemergence herbicidal activity of Compound A was evaluated with respect to the crop plants and weeds, by spraying a formulation of the test compound on the foliage of the young growing plants. In each series of tests, the plants were grown in narrow trays and sprayed with the formulation. The results of the tests were evaluated on the basis of the 0–9 scale described with respect to the earlier tests. The results of the tests are reported in Table I.

TABLE I

| | COMPOUND A | | | | | |
|---|---|---|---|---|---|---|
| | Rating of Effect at Indicated Dosage (lb/acre) | | | | | |
| | Preemergence | | | Postemergence | | |
| Plant Species | 0.25 | 1.0 | 4.0 | 0.25 | 1.0 | 4.0 |
| Corn | 2 | — | — | 0 | 0 | 0 |
| Cotton | 0 | 0 | 3 | 0 | 0 | 0 |
| Rice | 2 | 2 | 2 | 0 | 0 | 0 |
| Grain Sorghum | 2 | 5 | 4 | 0 | 0 | 0 |
| Soybean | 1 | 2 | 4 | 2 | 3 | 3 |
| Sugar Beet | 0 | 0 | 0 | 2 | 0 | 0 |
| Wheat | 4 | 4 | 3 | 0 | 0 | 0 |
| Barnyard Grass | 2 | 5 | 4 | 0 | 0 | 0 |
| Downy Brome | 0 | 2 | 3 | 0 | 0 | 0 |
| Wild Oats | 3 | 2 | 2 | 0 | 0 | 0 |
| Yellow Foxtail | 6 | 5 | 3 | 0 | 4 | 0 |
| Goose Grass | 0 | 0 | 0 | 0 | 2 | 0 |
| Yellow Nutsedge | — | — | 2 | — | — | 2 |
| Cocklebur | 0 | 0 | 0 | 0 | 0 | 0 |
| Morning Glory | 0 | 0 | 2 | 0 | 0 | 0 |
| Mustard | 2 | 2 | 0 | 0 | 0 | 0 |
| Pigweed | 2 | 3 | 2 | 0 | 0 | 0 |
| Sicklepod | 3 | 4 | 5 | 9 | 9 | 9 |
| Velvetleaf | 2 | 3 | 2 | 0 | 0 | 0 |

The sodium salt also was tested at the equivalent rate. The level and spectrum of activity of the salt were found to be essentially the same as that of the acid.

Compound A (as the erythro isomer of the diastereomer pair) also was formulated as the potassium, benzyl trimethylammonium and N-soya-propylenediamine salts. All were found to be essentially equivalent to the acid, at the equivalent rates of application.

We claim:
1. A method for controlling unwanted sicklepod plants which comprises subjecting the plants to an effective dosage of the (R*,S*)-(+)- optical isomer of 4-benzoyl-2,3-diphenylbutyric acid.

* * * * *